United States Patent [19]

Williams

[11] 4,072,570
[45] Feb. 7, 1978

[54] PREPARATION OF A TUBERCULOSIS TEST MEDIUM BY RECONSTITUTING A STORAGE STABILIZED DRY POWDERED LOWENSTEIN-JENSEN MEDIUM

[75] Inventor: Wilmore Williams, Chicago, Ill.

[73] Assignee: Beatrice Foods Co., Chicago, Ill.

[21] Appl. No.: 659,703

[22] Filed: Feb. 20, 1976

Related U.S. Application Data

[63] Continuation of Ser. No. 243,078, April 11, 1972, abandoned.

[51] Int. Cl.$^2$ .................................................. B01D 1/16
[52] U.S. Cl. .................................. 195/100; 195/102; 159/48 R; 159/DIG. 11; 426/614
[58] Field of Search ..................... 159/4, 48, DIG. 11; 195/100-102; 203/14, 17-19; 99/210

[56] References Cited

U.S. PATENT DOCUMENTS

| 2,476,412 | 7/1949 | Harris | 426/47 |
| 2,531,343 | 11/1950 | Patterson | 209/3 |
| 3,075,887 | 1/1963 | Silliker | 195/100 |
| 3,360,440 | 12/1967 | Haab | 195/102 |

*Primary Examiner*—Norman Yudkoff
*Assistant Examiner*—Martin G. Mullen
*Attorney, Agent, or Firm*—Murray & Whisenhunt

[57] ABSTRACT

A storage stable Lowenstein-Jensen medium is prepared by spray drying the liquid medium at an outlet temperature of up to 212° F to provide a powder having a moisture content of less than 9% by weight. The spray-dried powder is stable at ambient temperature for at least six months and may be easily reconstituted to the fluid Lowenstein-Jensen medium and used in testing for tuberculosis by simple mixing at ambient conditions.

4 Claims, No Drawings

PREPARATION OF A TUBERCULOSIS TEST MEDIUM BY RECONSTITUTING A STORAGE STABILIZED DRY POWDERED LOWENSTEIN-JENSEN MEDIUM

This is a continuation, of application Ser. No. 243,078 filed Apr. 11, 1972 and now abandoned.

The present invention relates to a stabilized growth medium for tuberculosis organisms, and more particularly to a stabilized medium which may be stored under ambient conditions for extended periods of time without degradation or other deterioration of the growth medium.

The detection of the disease tuberculosis has long been performed by culturing a specimen from a suspected host in a medium referred to in the art as the Lowenstein-Jensen medium, or modifications thereof. By allowing the sample to incubate for a set period of time in the Lowenstein-Jensen medium, the M. tuberculosis organisms will develop to the substantial exclusion of other organisms and a positive test for tuberculosis is therefore performed. While this test is quite accurate and is widely practiced, the test has a decided disadvantage in that the Lowenstein-Jensen medium is not storage stable at ambient temperatures and even when refrigerated must be used within 30 days of preparation. In view thereof, it has been the practice in the art to use the Lowenstein-Jensen medium within a relatively short period after preparation. Thus, it is necessary to frequently perform the time-consuming preparation of fresh medium. The time-consuming preparation has generally restricted the use of the Lowenstein-Jensen medium to organizations which would conduct numerous tuberculosis tests. The occasional tester or the smaller institution cannot economically test for tuberculosis, due to the difficulty and expense of frequently preparing fresh medium.

The basic ingredient in the Lowenstein-Jensen medium is fresh whole eggs, e.g., eggs no older than three days. The medium must be prepared in a specific manner with specific nutrient salts added to the fresh eggs, as is well known in the art. Once the medium has been prepared, it must be refrigerated and should be used within a relatively short time of preparation, as discussed above, or the results obtained therewith are questionable. Attempts in the art at extending the useful life of a prepared Lowenstein-Jensen medium have not met with success and the most common expedient is to premix the nutrient salts in a sterile manner and to place the fresh eggs in the salt mixture when the medium is to be prepared.

From the above, it is quite clear that a storage stable Lowenstein-Jensen medium would be quite advantageous in the art and that the art has long felt the need for a storage stable Lowenstein-Jensen medium. Accordingly, it is an object of the present invention to provide stabilized dry components of a Lowenstein-Jensen medium. It is a further object to provide such stabilized dry components for a Lowenstein-Jensen medium which can be stored at room temperature for substantial periods of time without significant deterioration thereof. It is yet another object of the invention to provide a method whereby the stabilized dry components for a Lowenstein-Jensen medium may be readily placed in a liquid and thereby made suitable for use in a tuberculosis test. Other objects will be apparent from the following disclosure and claims.

It has now been quite unexpectedly discovered that a Lowenstein-Jensen medium may be stabilized for sustained preservation by spray drying the medium in a conventional spray-dryer at temperatures consistent with not adversely affecting the protein content thereof.

The initial medium prepared for spray-drying will be the same as a conventional Lowenstein-Jensen medium. There are considerable numbers of specific procedures for preparing a Lowenstein-Jensen medium or a modification thereof. However, generally, fresh whole eggs are aseptically combined with nutrient salts, stabilizers, inhibitors, thickeners, etc., and mixed until a well-blended mixture is obtained. Thereafter, the mixture is inspissated at less than 80°–90° C for about 45 minutes. A commonly used procedure is that of cleaning fresh eggs in 5% soda and soap solution, rinsing thoroughly with water, aseptically breaking the eggs into a sterile flask containing glass beads, adding nutrients, salts etc., shaking to form a uniform mixture or emulsion, placing the mixture in test tubes and autoclaving the tubes in a slanted position at 80°–90° C for 45 minutes. Sterility is checked by incubating a test tube at 37° C. The test tubes are stored under refrigeration.

Irrespective of which specific procedure is used, and many are known to the art, after the Lowenstein-Jensen medium has been prepared, according to the present invention, it is introduced into a conventional spray-drying apparatus. Either a box-type dryer or a tower dryer may be used, since the important parameters are only the temperature of the spray-drying and the resulting moisture content of the powder so obtained. It is important that the medium be dried to a powder at such time and temperature combinations as to not adversely affect the protein of the medium.

As is generally practiced in the spray-drying art, the box or tower (chamber) of the spray dryer is kept at some relatively constant set of temperatures by means of heated gas passing therethrough. The fluid to be spray dried is atomized by a nozzle and sprayed into the chamber. The fluid may be, if desired, heated, e.g., up to temperatures at, or slightly above that of the spray-drying chamber. The temperature of the heated gas introduced into the spray dryer is referred to as the inlet temperature and the temperature of the gas leaving the spray dryer is referred to as the outlet temperature. In the present case, it has been found that the inlet temperature should be no higher than 300° F. More preferably, the inlet temperature should be somewhat less than 300° F, and temperatures between 230° F and 280° F., e.g. between 240° F and 280° F and particularly preferred. The outlet temperature in all cases must be less than 212° F and more preferably less than 200° F. Thus, temperatures between 140° F, especially 150° F, and 200° F are preferred. However, best results are obtained if the outlet temperature is between 160° F and 190° F and especially between 175° F and 185° F, e.g. 180° F. The fluid to be atomized and spray dried may be at a temperature up to 138° to 140° F, preferably room temperature or slightly higher. The particular apparatus for heating and atomizing the fluid is not critical, nor is the particular procedure for spray drying critical. Thus, any conventional spray-drying apparatus and procedure may be used.

The volume of the spray dryer should be so chosen in combination with the temperatures involved that the resulting spray-dried powder has a moisture content, on a weight basis, of no greater than 9%, and preferably less than 7%, e.g. less than about 6%. Generally speaking, moisture contents of between 5% and 7% by weight are suitable for the present invention.

The spray dried powder is recovered from the spray dryer in the conventional manner and may then be packaged in any container desired so long as the container prevents ambient contamination. Thus, the spray-dried powder may be simply packaged in plastic or glass jars, flexible film, blister packages, twisted plastic bag packages, foil packages, wax paper packages and the like. It is not required that the package be hermetically sealed or any like special consideration, but it is preferred that ambient contamination be substantially eliminated by the packaging method. The elimination of ambient contamination is not in connection with the stabilized Lowenstein-Jensen medium itself, but in connection with unknown organisms which might be introduced into the reconstituted powder when used in testing for tuberculosis. The dried and packaged powder need not be stored under special temperatures and ambient temperatures are quite acceptable therefor. However, extreme temperatures should be avoided for obvious reasons. Accordingly, it is preferred that the powder not be subjected to freezing temperatures, nor is it preferred that the powder be stored at temperatures above 120° F, preferably less than 115° F, although neither of these extreme temperatures will adversely affect the powder unless the powder remains at those extreme temperatures for prolonged periods. On the other hand, however, the powder may be stored for prolonged periods of time at ambient temperatures without significant deterioration thereof. Thus, the powder may be stored at ambient temperatures for up to one year or more without significant deterioration, although as a precautionary measure and as a safety factor, it is preferred that the powder be reconstituted and used within 8 to 10 months of the drying time.

The powder may be reconstituted simply by mixing with water. Of course, it is preferred that the mixing be under sterile conditions and that the water be both sterilized and distilled. However, inspissation at 80° C to 90° C for 1 hour may be used if desired. The amount of powder which is reconstituted in water can, of course, vary considerably, but it is preferred that the amount which is reconstituted correspond to that which will produce a level of solid as the original freshly prepared Lowenstein-Jensen medium. Thus, the solid content of the reconstituted medium can vary from as low as 10% to as high as 20% by weight, but the preferred solid content will be between about 11% and 17%, especially between 13% and 15%. Reconstitution can be accomplished without any special technique or equipment, and simple mixing is quite adequate. Thus, the dried powder and water may be simply hand mixed or mixed with a conventional laboratory stirrer until dissolution thereof takes place. The mixing may be at ambient temperatures or slightly depressed or elevated temperatures and no special consideration in this regard is required. Accordingly, temperatures above the freezing point of water and as high as 120° F can be used for preparing the reconstituted mixture. However, there is no special advantage obtained by such variation in the temperature of the water for reconstitution, and ambient water is quite satisfactory.

For purposes of the present specification, the Lowenstein-Jensen medium is defined as a medium for the growth of tuberculosis organisms (Mycobacterium tuberculosis) and consists essentially of fresh whole egg and nutrient salts. If desired, inhibitors, thickeners, dyes and like non-essential ingredients may be used. The specific nutrient salts and the ratio thereof with the fresh whole egg may vary, as is known in the art. Thus, any combination of fresh whole egg and nutrient salts suitable for growing tuberculosis organisms are intended to be embraced by the disclosure and claims of this specification. A typical Lowenstein-Jensen formulation, however, is as follows: up to about 3% salts, especially up to about 2% salts, and preferably about 1% salts, up to about 10% water for dispersing and dissolving the salts, more generally up to about 8% water, and very often about 5 to 6% water. However, additional water may be used if desired for easy dispersement and dissolution of the salts since this only goes to diluting the concentration of the Lowenstein-Jensen medium. However, too great of dilution is not preferred, and generally speaking, no more than 15% by weight of the medium will be added water. The remainder of the medium will be essentially fresh eggs, but if desired, other ingredients, such as inhibitors, thickeners, viscosity control agents and the like may be added. Thus, typically, the medium will also contain up to 7% of potato flour, especially up to 6% and more generally between 4 and 5%. Also, up to 4%, generally less than 2% of glycerol may be added. An inhibitor or a dye or a material which will function in both manners is also generally added to the medium. Thus, up to about 1% of an inhibitor and/or dye, more generally less than 1%, may be added to the medium. Usually about half a percent of an inhibitor/dye such as Malachite Green is used in a conventional Lowenstein-Jensen medium. The nutrient salts used in the medium generally contain magnesium and phosphorus, as well as potassium and the particular combination of these salts is not narrowly critical. However, as a typical example, monopotassium phosphate, magnesium sulfate, and magnesium citrate may be used. Also, typically, asparagine is used in a Lowenstein-Jensen medium. Asparagine is an alkaloid found in the sprouts of many weeds and has the formula $NH_2.CH_2.(COOH).(CH_2CONH_2).\ H_2O$. When all of the foregoing ingredients are used, as is typical in a Lowenstein-Jensen formula, it is convenient to suspend or dissolve the salts in the water to which has been added glycerol, if glycerol is used in the medium.

The invention will be illustrated by the following examples, but it is to be clearly understood that the invention is not limited thereto and is fully applicable to the foregoing disclosure.

EXAMPLE 1

Lowenstein-Jensen medium was prepared by mixing until uniformly blended the ingredients shown in Table 1 below. The procedure for mixing the ingredients was as follows: to the water, when used, was added the glycerol, when used, and the salts, when used, were dispersed therein. When water is not used, glycerol is not used and when water is not used, the salts and/or other ingredients are simply dispersed in the fresh eggs. Irrespective, after a mixture has been made, it is whipped until air bubbles are dispersed in the mixture, i.e., a frothy mixture is obtained. After mixing, the ingredients were spray dried in a conventional box-type spray dryer with the inlet-outlet temperature as indicated in the Table. To the spray-dried powder was mixed between ½ and 1% on a weight basis of finely divided silica of particle size between submicron and micron range (Syloid) to improve flowability of the spray-dried powder. Each of the spray-dried compositions obtained therefrom were reconstituted with water to prepare a reconstituted medium having the same proportions of solids as the medium from which the corresponding sample was spray dried. In each case, the reconstituted medium shows all of the properties of the original medium prior to spray drying.

TABLE I

| Weight % Of Ingredients | TEST NUMBER | | | | | |
|---|---|---|---|---|---|---|
| | 1 | 2 | 3 | 4 | 5 | 6 |
| Water | 5.45 | 0 | 0 | 0 | 5.45 | 5.45 |
| Malachite Green | .059 | .059 | .059 | .059 | .059 | .059 |
| Monopotassium phosphate | .365 | .365 | .365 | 0 | .365 | 0 |
| Magnesium sulfate | .035 | .035 | .035 | 0 | .035 | 0 |
| Magnesium citrate | .087 | .087 | .087 | 0 | .087 | 0 |
| Asparagine | .525 | .525 | .525 | 0 | .525 | 0 |
| Potato Flour | 4.38 | 4.38 | 0 | 0 | 0 | 4.38 |
| Glycerol | 1.75 | 0 | 0 | 0 | 0 | 0 |
| Fresh Eggs | BALANCE | | | | | |
| SPRAY DRYING CONDITIONS | | | | | | |
| Outlet Temp. °F | 180 | 160 | 170 | 185 | 190 | 195 |
| Inlet Temp. °F | 280 | 285 | 290 | 275 | 270 | 265 |

EXAMPLE 2

In order to demonstrate the prolonged storage properties of the spray-dried powder, 8 samples of Test Number 1, as indicated in Table 1, were stored in a tightly capped container for the periods of 1, 2, 3, 4, 5, 6, 10 and 12 months. At the end of each storage period, the sample for that period was reconstituted to provide a medium with the same solid content as was originally present in the medium prior to spray drying. Slants of each sample were tested by inoculating with tuberculosis organisms. At the end of an incubation period of 2 weeks, the samples were examined and each showed a positive culture of M. tuberculosis. Accordingly, this example illustrates that the present spray-dried medium can be stored for prolonged periods of time and thereafter easily reconstituted for ready use in testing for tuberculosis.

From the foregoing, it can be easily appreciated that the present invention provides a method of producing a storage stable Lowenstein-Jensen medium by preparing that medium and spray-drying the same in a spray-drying apparatus which has a chamber and a fluid inlet equipped with an atomizing nozzle. In the method, the outlet gas from the chamber is at temperatures less than 212° F, and the powder produced always has a moisture content of less than 9%, e.g., about 6.2%. However, preferably the outlet gas is maintained at temperatures between 150° F and 200° F and the moisture content is less than 7%. While not so important as the outlet temperature, the inlet gas temperature should be between 230° F and 300° F, but temperatures between 240° F and 280° F are preferred. With these latter temperatures, moisture content of the resulting powder of less than 7% are readily obtained.

In the preferred mode of the invention, the gas outlet temperature is between 160° F and 190° F, the gas inlet temperature is between 240° F and 280° F and the moisture content of the resulting powder is less than 7% by weight. The process produces an ambient storage stable, dry, powdered and water-reconstitutable Lowenstein-Jensen medium. The powder so produced is composed of spray-dried solids of a Lowenstein-Jensen medium wherein the solid have a moisture content of less than 9% and are water soluable (reconstitutable) at ambient temperatures. The powder will have a moisture content of, preferably, less than 7% and more preferably less than 6%. The powder will have been produced by a spray-drying process wherein the temperatures (gas inlet and outlet temperatures) are consistent with not causing substantial deterioration of the protein of the powder, as for example, denaturation, peptization and like degradation. The dry powder produced is characterized, mainly, by a storage life of at least 6 months under ambient conditions without significant deterioration of the powder.

It will be readily apparent to those skilled in the art that various modifications and changes can easily be accomplished within the framework and disclosure of the foregoing specification. Accordingly, such modifications and changes are intended as incorporated into the specification and the invention is limited only by the spirit and the scope of the following claims.

What I claim is:

1. A method for producing a tuberculoses test medium from a reconstituted dry powdered, storage stabilized Lowenstein-Jensen medium comprising preparing a Lowenstein-Jensen medium which includes fresh whole eggs, nutrient salts and stabilizers, spray drying the medium in a spray dryer at an inlet temperature of between 230° F and 280° F and an outlet temperature of between 160° F and 190° F and under dryer conditions consistent with providing the dried powder with a moisture content of less than 9% by weight, recovering and packaging the dried powder, storing the packaged powder under ambient conditions, forming a reconstituted medium having a solids content of between 10–20% by weight from said powder, and inspissating said reconstituted medium to provide a medium used in testing for tuberculoses.

2. A method according to claim 1 wherein the said moisture content of said dried powder is less than 7% by weight.

3. A method according to claim 1 wherein the outlet temperature is between 160° and 190° F, the inlet temperature is between 240° and 280° F and the moisture content is less than 7% by weight.

4. The reconstituted Lowenstein-Jensen tuberculoses test medium produced by the method of claim 1.

* * * * *